United States Patent
Wahlgren et al.

(10) Patent No.: US 8,170,683 B2
(45) Date of Patent: *May 1, 2012

(54) DERMATOME STIMULATION DEVICES AND METHODS

(75) Inventors: Stephen B. Wahlgren, Easton, PA (US); Michael Tracey, Branchburg, NJ (US); Anthony DiUbaldi, Jackson, NJ (US)

(73) Assignee: Ethicon, Inc., Somerville, NJ (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/957,240

(22) Filed: Dec. 14, 2007

(65) Prior Publication Data
US 2009/0157149 A1    Jun. 18, 2009

(51) Int. Cl.
*A61N 1/00* (2006.01)
(52) U.S. Cl. ........................................... 607/66
(58) Field of Classification Search ............... 607/66
See application file for complete search history.

(56) References Cited

U.S. PATENT DOCUMENTS

| | | | |
|---|---|---|---|
| 4,406,288 A | 9/1983 | Horwinski | |
| 4,537,195 A | 8/1985 | McDonnell | |
| 4,719,922 A | 1/1988 | Padjen | |
| 4,989,605 A | 2/1991 | Rossen | |
| 5,421,817 A | 6/1995 | Liss et al. | |
| 5,562,717 A | 10/1996 | Tippey | |
| 5,702,428 A | 12/1997 | Tippey | |
| 5,851,223 A * | 12/1998 | Liss et al. | 607/46 |
| 6,035,236 A | 3/2000 | Jarding et al. | |
| 2003/0233137 A1 | 12/2003 | Paul | |
| 2005/0277998 A1 | 12/2005 | Tracey | |
| 2006/0047325 A1 | 3/2006 | Thimineur et al. | |
| 2006/0095090 A1 | 5/2006 | De Ridder | |
| 2006/0195146 A1 | 8/2006 | Tracey et al. | |
| 2006/0195153 A1 | 8/2006 | DiUbaldi | |
| 2007/0185541 A1 | 8/2007 | Di Ubaldi et al. | |
| 2008/0132962 A1 | 6/2008 | Di Ubaldi et al. | |

FOREIGN PATENT DOCUMENTS
DE        100 33 400 A1    1/2001
* cited by examiner

*Primary Examiner* — Eric D. Bertram
(74) *Attorney, Agent, or Firm* — Cheryl F. Cohen, LLC

(57) ABSTRACT

A nerve stimulation device includes a first waveform generator adapted to generate a first waveform having a first frequency capable of stimulating nerves within a dermatome, a second waveform generator adapted to generate a first carrier waveform having a second frequency capable of passing through tissue of a mammal, and a third waveform generator adapted to generate a second carrier waveform having a third frequency different than the second frequency and being capable of passing through the tissue of the mammal. The device includes a modulator electrically coupled to the first, second and third waveform generators and adapted to modulate the first waveform, the first carrier waveform, and the second carrier waveform to generate a modulated signal package capable of stimulating the nerves at different depths within the dermatome. The device also has an electrode electrically coupled to the modulator for applying the modulated waveform to the dermatomic region.

24 Claims, 13 Drawing Sheets

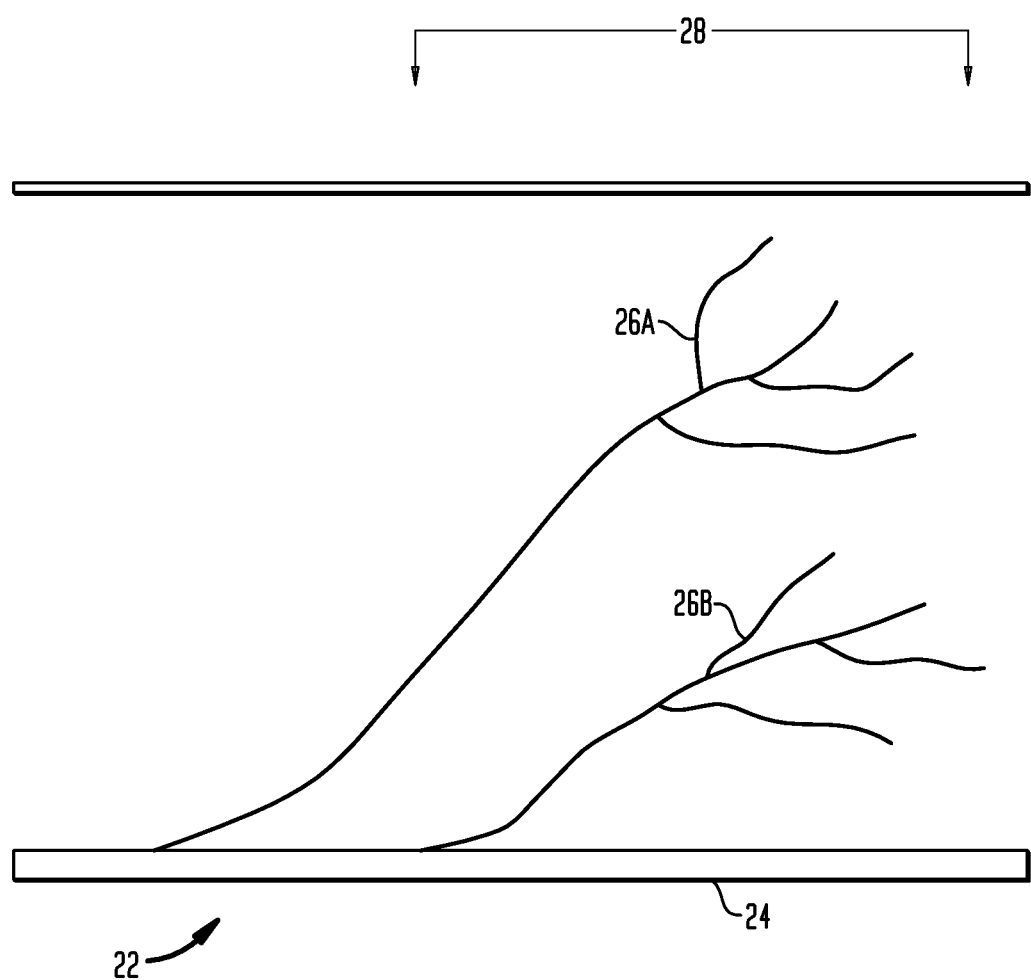

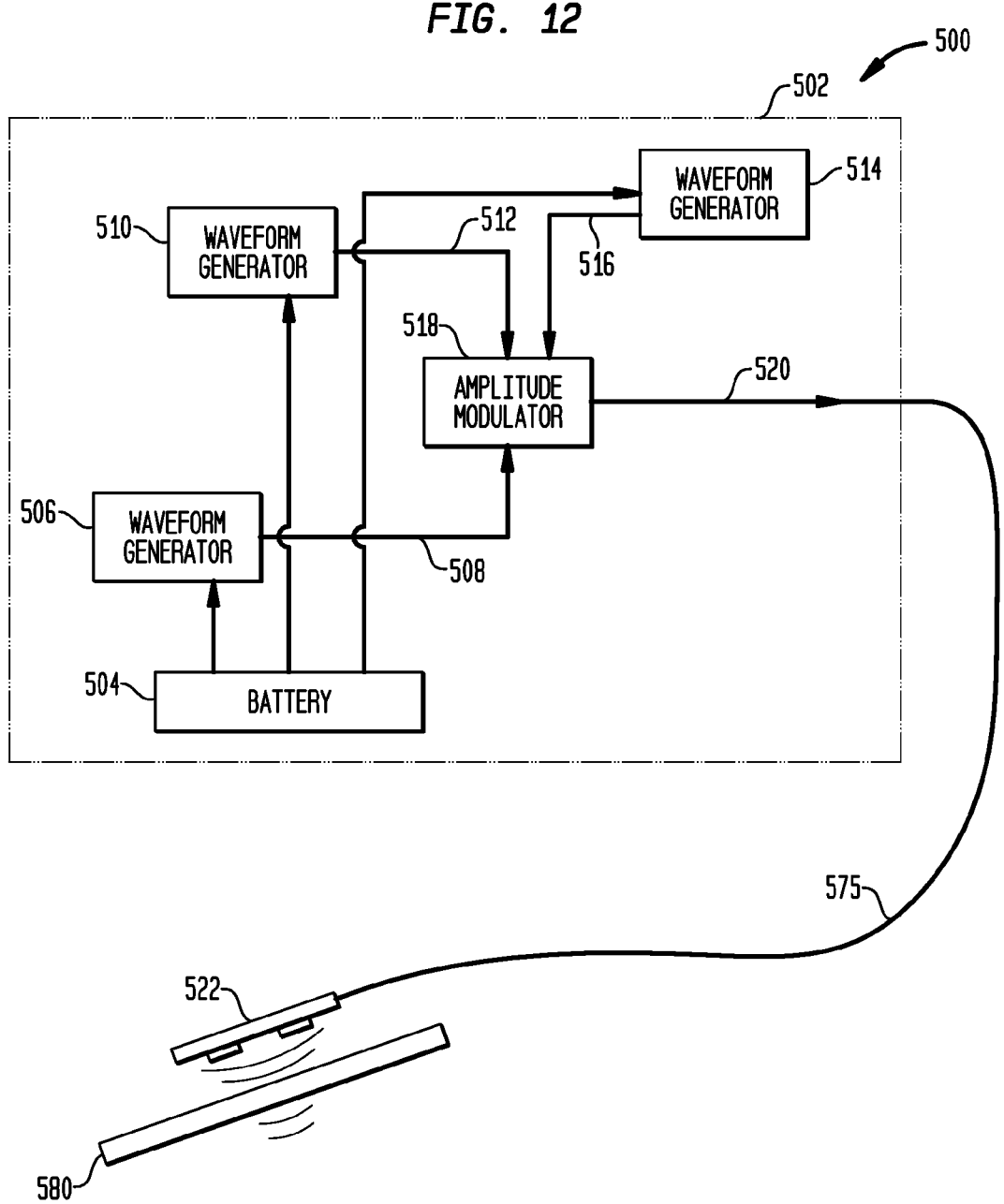

DERMATOME STIMULATION DEVICES AND METHODS

BACKGROUND OF THE INVENTION

1. Field of the Invention

The present invention is generally related to stimulating nerves and body parts. More specifically, the present invention is related to nerve stimulation devices used for stimulating target nerves and body parts to achieve therapeutic results.

2. Description of the Related Art

There are a wide variety of medical conditions that may affect an individual's health and well-being, and many treatment options have been developed to help physicians treat such conditions. While the number of treatment options has increased, such options are often merely palliative, i.e., relieving symptoms rather than actually curing the underlying condition. In fact, treatment protocols effectively targeting the underlying cause of a condition are quite rare.

A common medical condition is obesity, which often results from an imbalance between food intake and energy expenditure. Severe weight loss and abnormal loss of appetite is an equally serious condition that can lead to suffering and death. The most familiar example is anorexia nervosa, a condition that classically affects young women and is associated with pathologic alterations of hypothalamic and pituitary gland function.

Another adverse medical condition is fecal incontinence, which involves the loss of voluntary control to retain feces in the rectum. Fecal incontinence may result from a number of causes, such as old age, disease or trauma. Still another condition is urinary incontinence. One type of urinary incontinence is urge incontinence, which appears to be neurologically based and generally revealed as detrusor muscle instability or "bladder spasms."

A wide variety of therapies exist for treating the above medical conditions. One therapy involves behavior modification such as reducing food intake and increasing exercise. Another option involves using pharmacologic agents, for example to control appetite and increase energy expenditure. A third option involves surgery such as gastric bypass surgery and gastric banding. Although these treatment options may be very effective in treating one or more of the above-described conditions, they may be highly invasive, require significant lifestyle changes, and result in severe complications.

There have been a number of attempts to treat the above conditions using transcutaneous electrical nerve stimulation systems, commonly referred to as TENS. TENS devices are extremely invasive because they have electrode leads that must be implanted inside a patient, in close proximity to a target nerve (e.g. a sacral nerve). Another disadvantage with TENS is a limitation on the depth to which a low frequency stimulation signal (such as those needed to stimulate the pudendal and/or sacral nerves) can be driven due to tissue impedance and resulting signal dissipation, and without causing significant discomfort to a patient. Still another disadvantage with TENS is the limited effectiveness of higher frequency signals in stimulating nerves. As a result, TENS devices are unable to achieve deep nerve stimulation without the application of current intensities that are too high to be tolerated by patients for extended periods of time, if at all. For these reasons, despite the availability of TENS for well over 25 years, there has yet to be a commercially successful application of TENS for deeper nerve stimulation.

In some nerve stimulation devices, it has been observed that the generated electric field spreads widely, affecting untargeted muscles and nerves along with the target nerve. The wide spreading of the electric field significantly reduces the strength of the electrical signal at the target nerve. In order to properly stimulate the target nerve, the strength of the electrical signal must be substantially increased. This requires the devices to draw more power from the battery.

In other nerve stimulation devices, it has been observed that tissue impedance prevents the generated electric field from passing deeply into the tissue. As a result, the generated electric field is able to penetrate only the top layers of the epidermis, and is unable to pass deeply into the tissue to stimulate nerves located deeper in the tissue.

Thus, there remains a need for improved devices and methods of stimulating body parts and nerves. In particular, there remains a need for improved nerve stimulation devices that effectively stimulate target nerves and body parts, while not stimulating untargeted nerves and body parts. Furthermore, there remains a need for nerve stimulation devices that are less invasive, and that require less power to operate effectively, thereby minimizing the need to replace and/or recharge power sources. There also remains a need for nerve stimulation devices that are capable of stimulating nerves located deeper within body tissue, while minimizing power and size requirements. In addition, there remains a need for devices and methods that are able to effectively stimulate nerves using less power.

SUMMARY OF THE INVENTION

In one embodiment, the present invention is directed to nerve stimulation devices that stimulate nerves in a more efficacious and non-invasive manner, such as the devices and methods disclosed in commonly assigned U.S. Patent Publication Nos. US 2005/0277998, filed Jun. 7, 2005 ("the '998 publication"), and US 2006/0195153, filed Jan. 31, 2006 ("the '153 publication"), the disclosures of which are hereby incorporated by reference herein. In one or more embodiments thereof, the '998 and '153 publications teach non-invasive, transcutaneous neurostimulation devices that generate and transmit a controlled, amplitude-modulated waveform comprising a carrier signal and a pulse envelope. The carrier waveform is designed to be of sufficient frequency to overcome attenuation due to tissue impedances. The pulse envelope contains specific pulse width, amplitude and shape information designed to stimulate specific nerves. The devices and methods disclosed in the '998 and '153 publications are capable of generating modulated waveforms that effectively stimulate target nerves, but do not stimulate untargeted peripheral nerves and body parts. Moreover, the devices and methods disclosed in the '998 and '153 publications are able to effectively stimulate nerves located deeper within body tissue.

In one embodiment, the present invention discloses a device and method for stimulating a predetermined nerve ending or sensory nerve fibers residing within the skin of a mammal within a specific dermatome. This device includes a first waveform having a frequency capable of stimulating a predetermined nerve of the mammal, a second waveform generator adapted to generate a carrier waveform having a frequency capable of passing through tissue of the mammal, a third waveform generator adapted to generate another carrier waveform having a frequency capable of passing through tissue of the mammal, a modulation device electrically coupled to the first, second and third waveform generators and adapted to modulate the first and carrier waveforms to create a modulated waveform, and an electrode electrically coupled to the modulation device and positioned substantially adjacent to skin of the mammal, and adapted to apply the modulated waveform thereto. The carrier waveforms are transmitted simultaneously within a single pulse envelope. The first waveform has a frequency substantially within the range of 10-40 Hz, and may be a square wave, although other shapes may be used. The carrier waveforms may have frequencies substantially within the range of 10-400 kHz, and may be sinusoidal waveforms. The carrier waveforms preferably have frequencies that are different from one another. In other embodiments, three or more carrier waveforms may be generated for carrying the nerve stimulating signals to various tissue depths within the dermatome for stimulating nerves or nerve endings located at three or more depths.

In one embodiment of the present invention, a nerve stimulation device includes a first waveform generator adapted to generate a first waveform having a first frequency capable of stimulating nerves within a dermatome, a second waveform generator adapted to generate a first carrier waveform having a second frequency capable of passing through tissue of a mammal, and a third waveform generator adapted to generate a second carrier waveform having a third frequency different than the second frequency and being capable of passing through the tissue of the mammal. The device desirably includes a modulator electrically coupled to the first, second and third waveform generators that is adapted to modulate the first waveform, the first carrier waveform, and the second carrier waveform to generate a modulated signal package capable of stimulating the nerves at different depths within the dermatome. The device also desirably includes an electrode electrically coupled to the modulator for applying the modulated waveform to the dermatome. In one embodiment, the device may include a fourth waveform generator adapted to generate a third carrier waveform having a fourth frequency capable of passing through the tissue of the mammal. In this embodiment, the modulator is electrically coupled to the fourth waveform generator to generate the modulated signal package.

In one embodiment, the first frequency of the first waveform is about 10-200 Hz. In one embodiment, the second frequency of the first carrier waveform is about 10-400 KHz, and more preferably about 200 KHz. In one embodiment, the third frequency of the second carrier waveform is about 10-400 KHz, and more preferably about 300 KHz. The first and second carrier waveforms preferably have different frequencies so that they carry the first nerve stimulating waveform to different depths within the dermatome.

The nerve stimulation device may include a transcutaneous nerve stimulation patch securable over the skin of a mammal, such as a human. In one embodiment, the nerve stimulation device may include an electrode implantable in the mammal. In one embodiment, the nerve stimulation device may include an implantable pulse generator including an implantable housing. The housing preferably contains the waveform generators, the modulator, and the power supply.

In one embodiment of the present invention, a nerve stimulation device includes a first system having a first waveform generator adapted to generate a first waveform having a first frequency capable of stimulating nerves within a dermatome, a second waveform generator adapted to generate a first carrier waveform having a second frequency capable of passing through tissue of a mammal, a first modulator electrically coupled to the first and second waveform generators and adapted to modulate the first waveform, and the first carrier waveform to generate a first modulated waveform. The device preferably includes a second system including a third waveform generator adapted to generate a second waveform having a third frequency that equals the first frequency of the first waveform and that is capable of stimulating the nerves within the dermatome, a fourth waveform generator adapted to generate a second carrier waveform having a fourth frequency that differs from the second frequency and that is capable of passing through the tissue of the mammal, and a second modulator electrically coupled to the third and fourth waveform generators and adapted to modulate the second waveform, and the second carrier waveform to generate a second modulated waveform. The device also desirably includes an electrode electrically coupled to the modulator for applying the first and second modulated waveforms, whereby the first and second modulated waveforms are adapted to pass through the tissue at different depths for stimulating the nerves at different depths within the tissue.

In one embodiment of the present invention, a method of stimulating nerves within a dermatome to different depths includes generating a first waveform having a first frequency capable of stimulating the nerves within the dermatome, generating a first carrier waveform having a second frequency capable of passing through tissue within the dermatome, and generating a second carrier waveform having a third frequency different than the second frequency and being capable of passing through the tissue within the dermatome. The method desirably includes combining the first waveform, the first carrier waveform, and the second carrier waveform to generate a modulated signal package capable of stimulating the nerves at two different depths within the dermatome, and applying the modulated waveform to the dermatome for stimulating the nerves within the dermatome.

In one embodiment, a method may include generating a third carrier waveform having a fourth frequency different than the second and third frequencies and being capable of passing through the tissue within the dermatome, and combining the third carrier waveform with the first waveform, the first carrier waveform, and the second carrier waveform to generate a second modulated signal package capable of stimulating the nerves at three different depths within the dermatome. In one embodiment, the first waveform, the first carrier waveform, and the second carrier waveform are generated simultaneously. In another embodiment, the first carrier waveform and the second carrier waveform are generated exclusively of one another.

In one embodiment, the first frequency of the first waveform is about 10-200 Hz, the second frequency of the first carrier waveform is about 10-400 KHz, and the third frequency of the second carrier waveform is about 10-400 KHz. The first carrier waveform carries the first waveform to a first depth within the dermatome and the second carrier waveform carries the first waveform to a second depth within the dermatome.

In one embodiment, the waveform generators and the electrodes may be positioned within a patch device having an adhesive thereon for securing the patch to the skin. In one embodiment, the predetermined nerve endings may be sympathetic afferent nerves at the T5-T9 dermatome, and the patch may be positioned substantially at the thoracic regions of a mammal's body for stimulation of the celiac ganglia of the sympathetic nervous system. This nerve stimulation technique may be used for treatment of obesity. In another embodiment, the predetermined nerve is the S1, S2, and S3 afferent parasympathetic pathways to the spinal cord, and the patch is positioned substantially at the sacral regions of the mammal's body. This nerve stimulation technique may be used for treatment of fecal and/or urinary incontinence.

The present invention also provides a method for stimulating a dermatome of a mammal. In one embodiment, the method includes generating a waveform having a frequency capable of stimulating the dermatome, and applying the signal to the mammal's skin. In another embodiment, this method includes generating a first waveform having a frequency capable of stimulating the dermatome, generating a pair of carrier waveforms having distinct frequencies capable of passing through the tissue of a mammal, modulating the first waveform with the two carrier waveforms to produce a modulated signal, and applying the modulated signal to the tissue of the mammal.

These and other preferred embodiments of the present invention will be described in more detail below.

BRIEF DESCRIPTION OF THE DRAWING

FIG. 2 shows a nerve with nerve endings extending through tissue of a mammal.

FIG. 12 shows a schematic illustration of a nerve stimulation device, in accordance with another embodiment of the present invention.

DETAILED DESCRIPTION

Figure 1A:
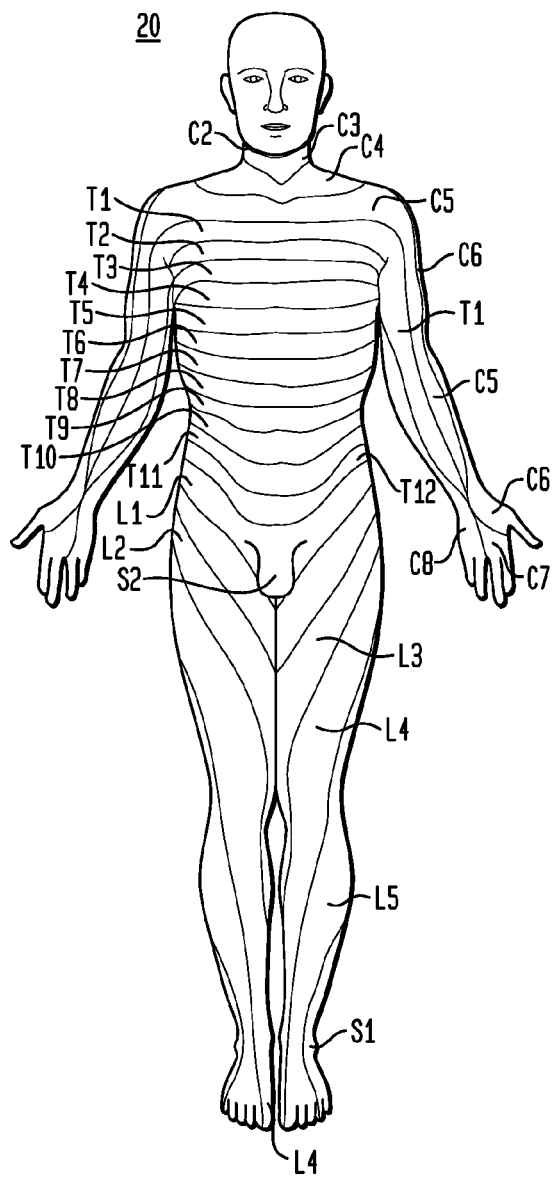
FIGS. 1A and 1B show the dermatome regions present on a human body.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Figure 1B:
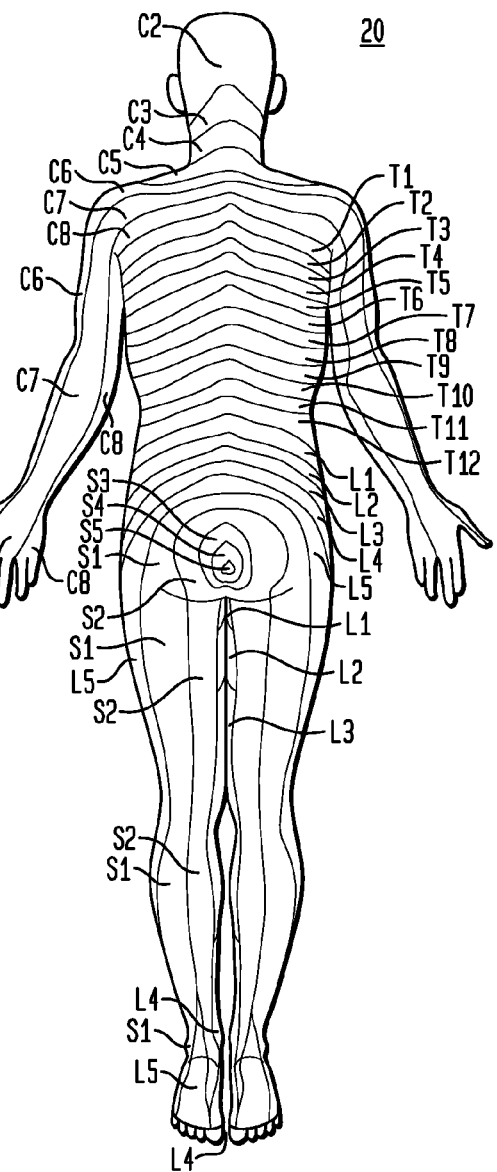

Referring to FIGS. 1A and 1B, a dermatomic region is an area of a body that has sensory afferent nerve fibers emanating from a single dorsal root. FIGS. 1A and 1B depict the dermatomes that form consecutive bands on the skin surface of a human body. FIG. 1A shows an anterior view of the human body, and FIG. 1B shows a posterior view of the human body. Referring to FIG. 2, the dorsal root 22 is the afferent sensory root of a spinal nerve. At the distal end 24 of the dorsal root 22 is the dorsal root ganglion 26A, 26B, which contains the neuron cell bodies of the nerve fibers conveyed by the root 22. These fibers make up a dermatomic region 28. Stimulation of the nerve endings 26A, 26B within a specific dermatomic region 28 results in transmission of sensory information via afferent nerves to the spinal cord and brain. The transmission of this sensory information may be used to treat certain conditions such as obesity and incontinence.

Figure 3A:
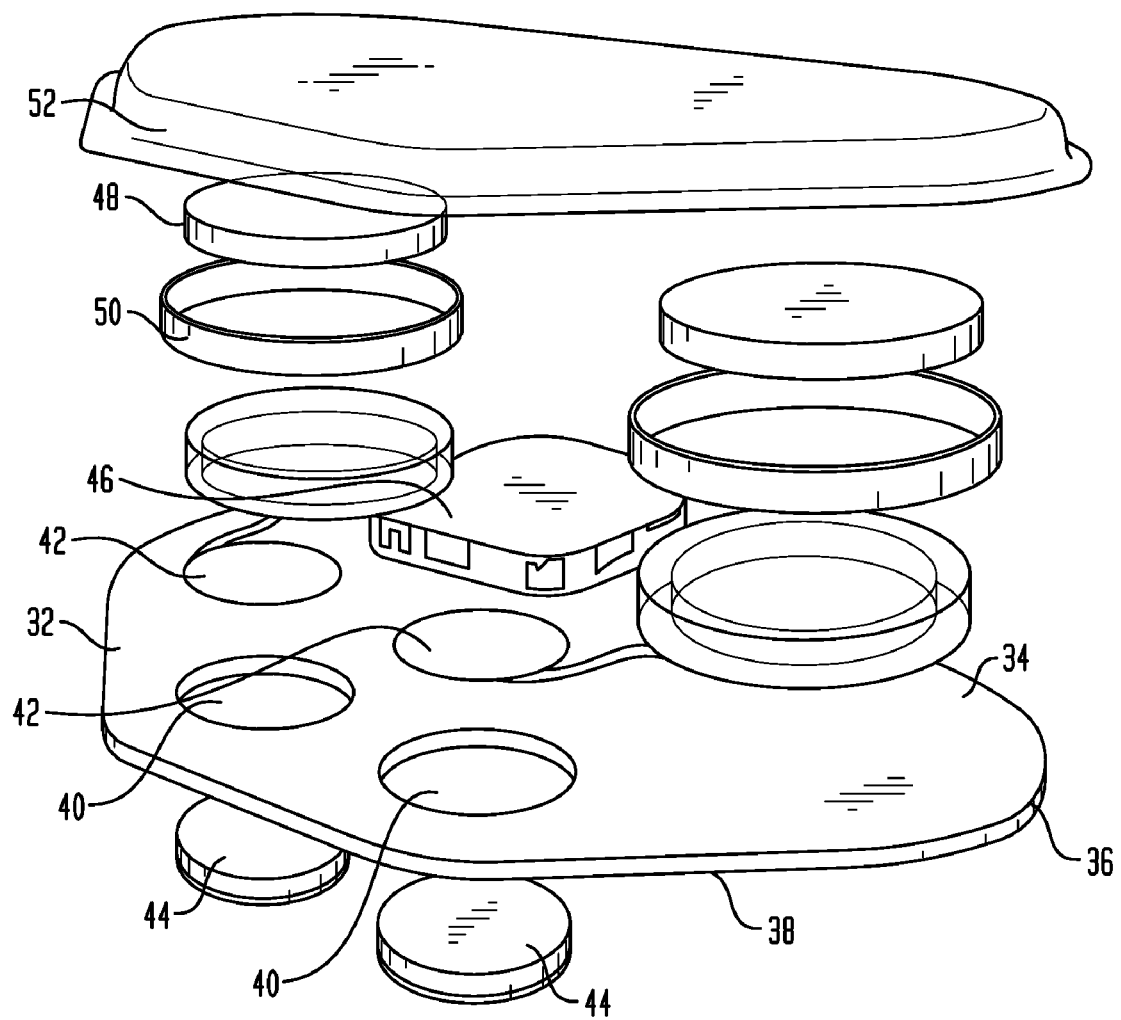
FIG. 3A shows an exploded view of a nerve stimulation patch, in accordance with one embodiment of the present invention.
Figure 3B:
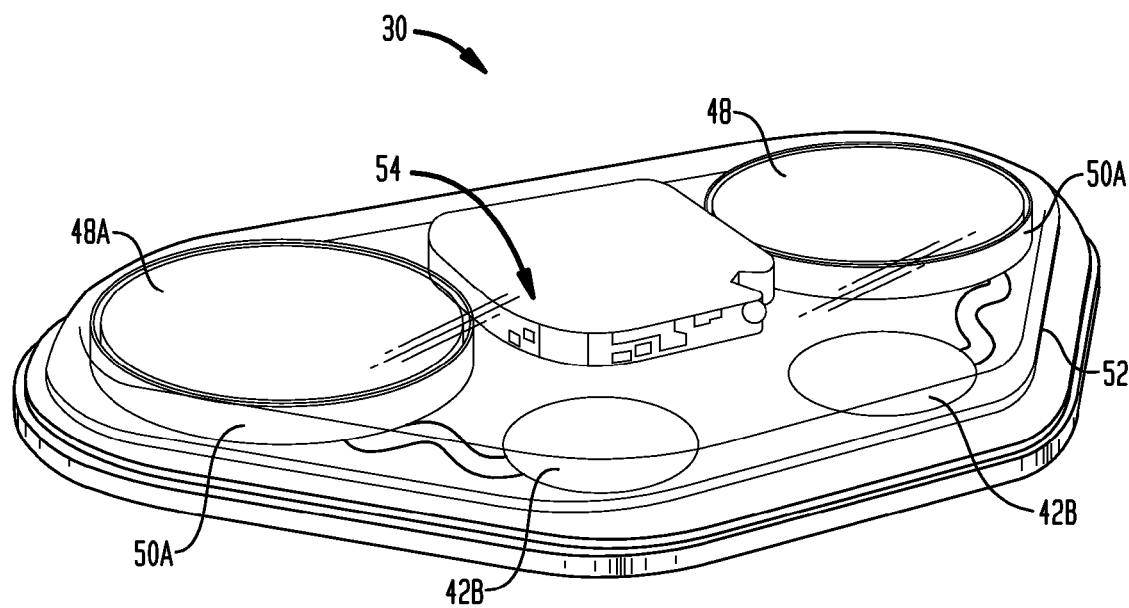
FIG. 3B shows the nerve stimulation patch of FIG. 3A after assembly.

FIGS. 3A and 3B show a nerve stimulation device 30, in accordance with one embodiment of the present invention. The nerve stimulation device 30 includes a first layer 32 having a top surface 34 and a bottom surface 36. The bottom surface 36 of the first layer 32 is covered by an adhesive layer 38 having openings 40A, 40B extending therethrough that accommodate active and return integrated electrodes 42A, 42B. The adhesive layer 38 includes the holes that accommodate the shape of the electrodes 42A, 42B and allow direct contact of the electrodes with the surface of a patient's skin. The device 30 includes electrolyte pads 44A, 44B that cover the respective electrodes 42A, 42B. The electrodes 42A, 42B may be secured directly to the first layer 32, or may be held in place by a second layer comprised of any suitable material such as plastic. The integrated electrodes may be gold-plated or made of other corrosion-resistant metals. The device 30 includes a third layer 46 of a flexible electronics board or flex board that contains all of the electronic elements described in the '998 publication and that is electrically coupled to the electrodes 42A, 42B. The flexible board 46 has parts that are folded over the batteries to complete battery connections and to nest the electronic components into a more compact space. A fourth layer is a thin film battery 48 of any suitable size and shape that can be held in place by a battery seal or ring 50, and the top cover 52 is any suitable covering such as the plastic coverings commonly used in bandages.

Referring to FIG. 3B, the nerve stimulating device 30 includes a photodiode 54 underlying a section of the top layer, which can be used as an extremely low-power communication receiver. The photodiode is small, inexpensive, consumes zero power when inactive, and is much more energy and space-efficient than an RE link. In other embodiments, however, an RE link may be used. The device 30 includes electrodes 42A, 42B powered by batteries 48A, 48B, which are surrounded by battery seals 50A, 50B. The two stimulation electrodes 42A, 42B are shifted off to one side, resulting in a somewhat D-shaped device. The top cover 52 is water resistant for protecting the internal components during typical activities such as washing, bathing and showering.

Figure 4:
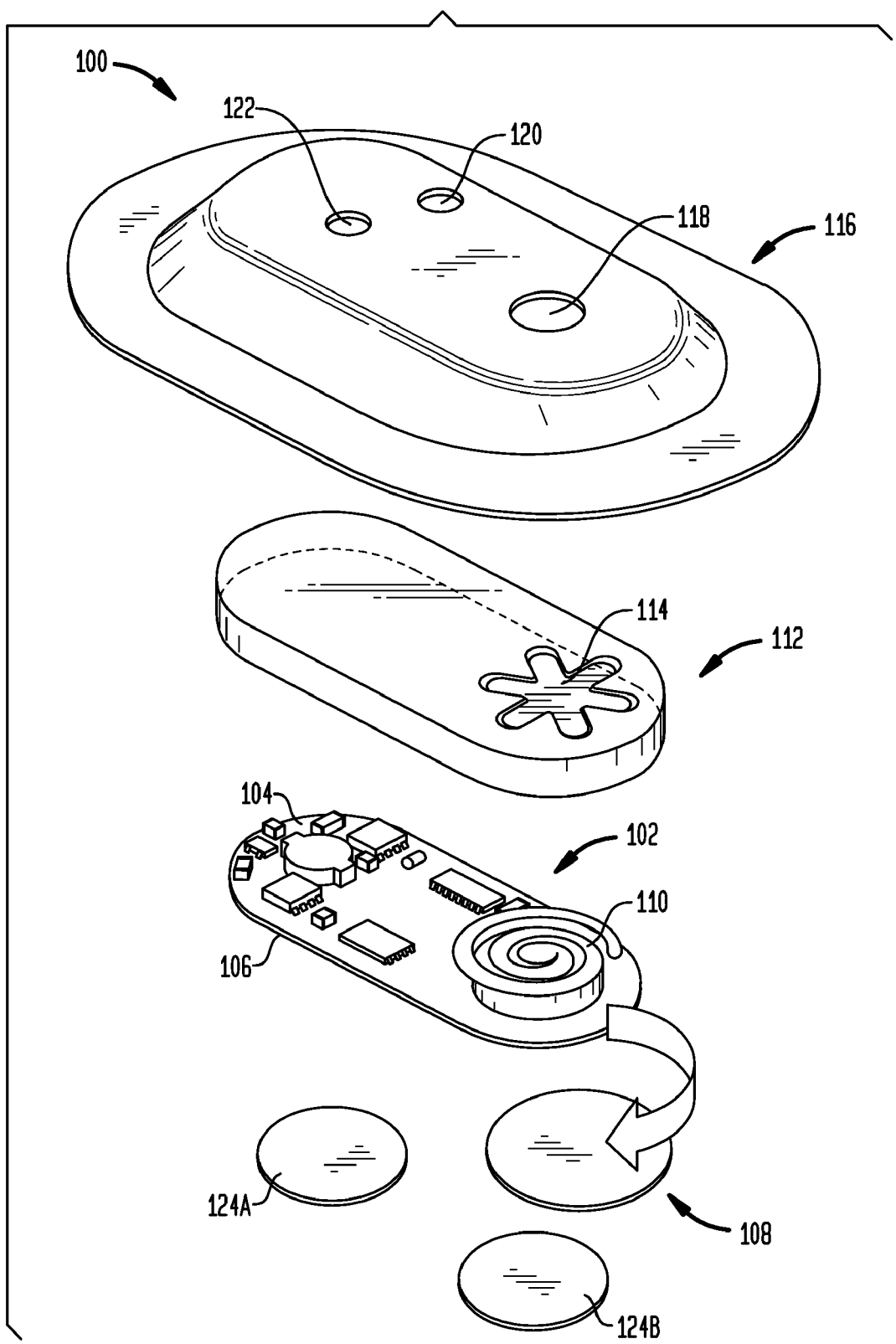
FIG. 4 shows an exploded view of a nerve stimulation patch, in accordance with another embodiment of the present invention.

In one embodiment of the present invention, a nerve stimulation patch may include one or more of the elements disclosed in commonly assigned U.S. patent application Ser. No. 11/941,508, filed Nov. 16, 2007, entitled, "Nerve Stimulation Patches and Methods for Stimulating Selected Nerves," the disclosure of which is hereby incorporated by reference herein. Referring to FIG. 4, the nerve stimulation patch 100 includes a substrate 102, such as a circuitized substrate, having a top surface 104 and a bottom surface 106. The circuitized substrate 102 has components mounted thereon that are adapted to generate electrical signals that may be applied to a body to stimulate one or more selected nerves. In one embodiment, the circuitized substrate 102 has active and passive components that generate electrical signals, modulate the signals and apply the signals to a body for stimulating selected nerves.

The selective nerve stimulation patch 100 includes a power source 108, such as a battery, that provides a source of energy for the patch. In one embodiment, the power source 108 is preferably secured over the top surface 104 of the substrate, and underlies a conductor 110. The patch 100 desirably includes a conductive adhesive (not shown) provided between the conductor 110 and the top surface of the power source 108. In one embodiment, the conductor 110 is part of a single-use or one-time use switch that when activated, permanently connects the power source 108 to the components on the circuitized substrate 102. Initially, the conductor 110 is preferably spaced and isolated from the power source 108. When the conductor 110 is squeezed toward the top surface of the power source, the conductor adheres to the power source (via the conductive adhesive) to provide power for the circuitized substrate and the components attached to the circuitized substrate. The conductor 110 is preferably flexible. In one embodiment, the conductor is a spiral conductor.

The selective nerve stimulation patch 100 preferably includes a molded top cap 112 that is assembled over the circuitized substrate 102. The molded top cap 112 is preferably transparent so that optical signals can pass through the molded top cap, as will be described in more detail below. One end of the molded top cap 112 desirably has a weakened region 114 formed therein that is depressible for pressing the conductor 110 against the top of the battery 108. In other embodiments, the molded top cap 112 may have a uniform thickness throughout the length of the top cap. The molded top cap 112 preferably conforms to the shape of the underlying circuitized substrate 102. In one embodiment, the top cap 112 is formed atop the substrate 102 using injection molding techniques. The molded top cap may comprise an encapsulant material that is curable. In another embodiment, the molded top cap 112 may be formed as a separate part that is assembled with the circuitized substrate.

The selective nerve stimulation patch 100 also has a top cover 116 overlying the top cap 112 and the circuitized substrate 102. In one embodiment, the top cover 116 is made of a waterproof, breathable material, such as the material sold under the trademark GORE-TEX. The top cover 116 desirably has a first opening 118 aligned with the conductor 110, a second opening 120 aligned with a LED provided on the substrate, and a third opening 122 aligned with an optical switch such as a photodiode for adjusting the parameters of an output signal or waveform generated by the patch 100.

The selective nerve stimulation patch 100 also includes electrodes (not shown) accessible at the bottom surface 106 of the circuitized substrate 102, and adhesive, conductive pads 124A, 124B that overlie the respective electrodes. In one embodiment, the electrodes are disposed with the substrate and are accessible at the bottom surface of the substrate. Providing the electrodes at the bottom surface of the circuitized substrate minimizes the size and/or footprint of the patch 100. This structure also reduces the number of parts required for making a nerve stimulation patch.

Figure 5:
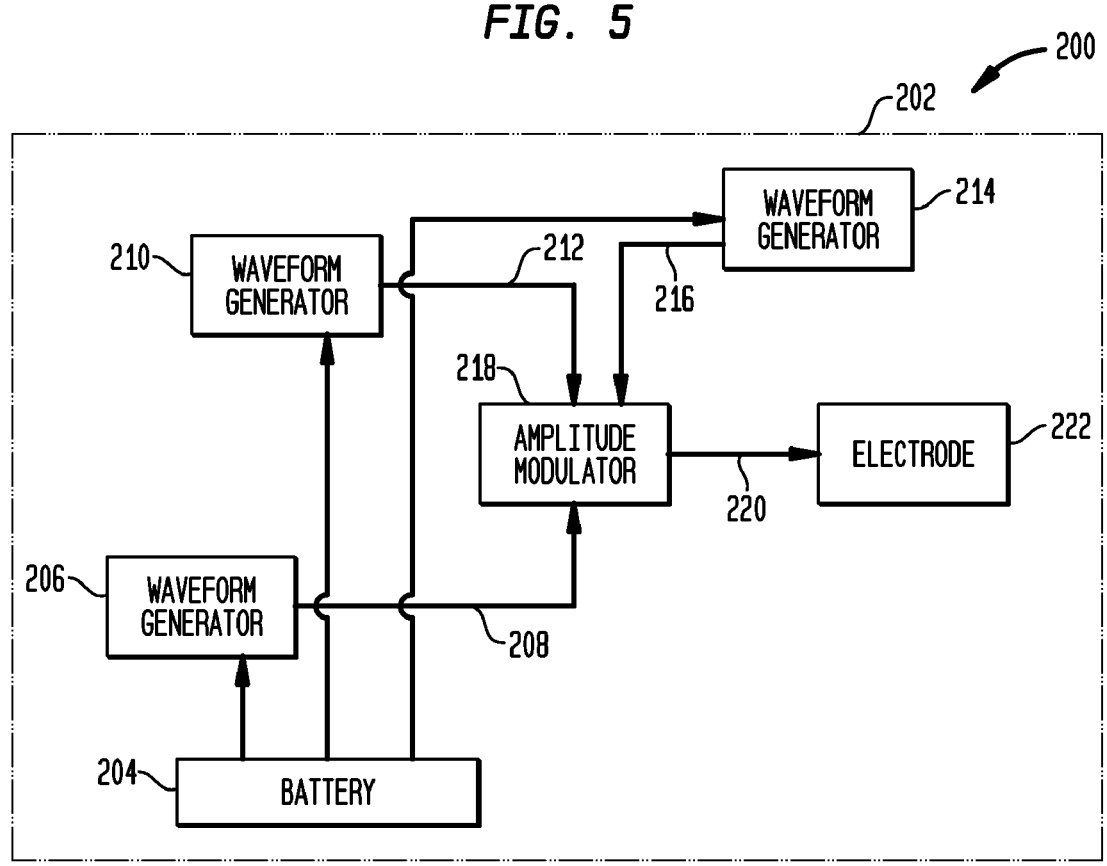
FIG. 5 shows a schematic illustration of a nerve stimulation device capable of stimulating nerves at different depths, in accordance with one embodiment of the present invention.

Referring to FIG. 5, in one embodiment of the present invention, a nerve stimulation device 200, such as a nerve stimulation patch, includes a circuitized substrate 202 having components provided thereon for generating electrical signals for stimulating target nerves. The nerve stimulation patch 200 includes a suitable power source 204, such as a lithium ion battery, a first waveform generator 206 that produces a first waveform 208 having a relatively low frequency capable of stimulating target nerves or nerve endings, a second waveform generator 210 that produces a second waveform 212 having a relatively high frequency capable of passing through the tissue of a mammal, and a third waveform generator 214 that produces a third waveform 216 having a relatively high frequency capable of passing through the tissue of a mammal. The second and third waveforms preferably generate carrier waveforms having different frequencies for passing to different depths in the tissue. The first, second, and third waveform generators 206, 210, and 214 are preferably electrically coupled to and powered by the battery 204. These waveform generators may be of any suitable type, such as those sold by Texas Instruments of Dallas, Tex. under model number NE555. The outputs of the respective first 206, second 210 and third 214 waveform generators are applied to an amplitude modulator 218, which modulates the three waveforms into a modulated signal package 220. The term "signal package" is used herein to describe a single output signal consisting or two or more individual signals modulated together in any way. In one embodiment, the two carrier waveforms 212, 216 are combined (see FIG. 6B), and the combined waveforms are further modulated by the low frequency first waveform 208 to produce a nerve stimulating signal 220 (see FIG. 7) that is capable of reaching different depths of the tissue of a mammal.

Figure 6A:
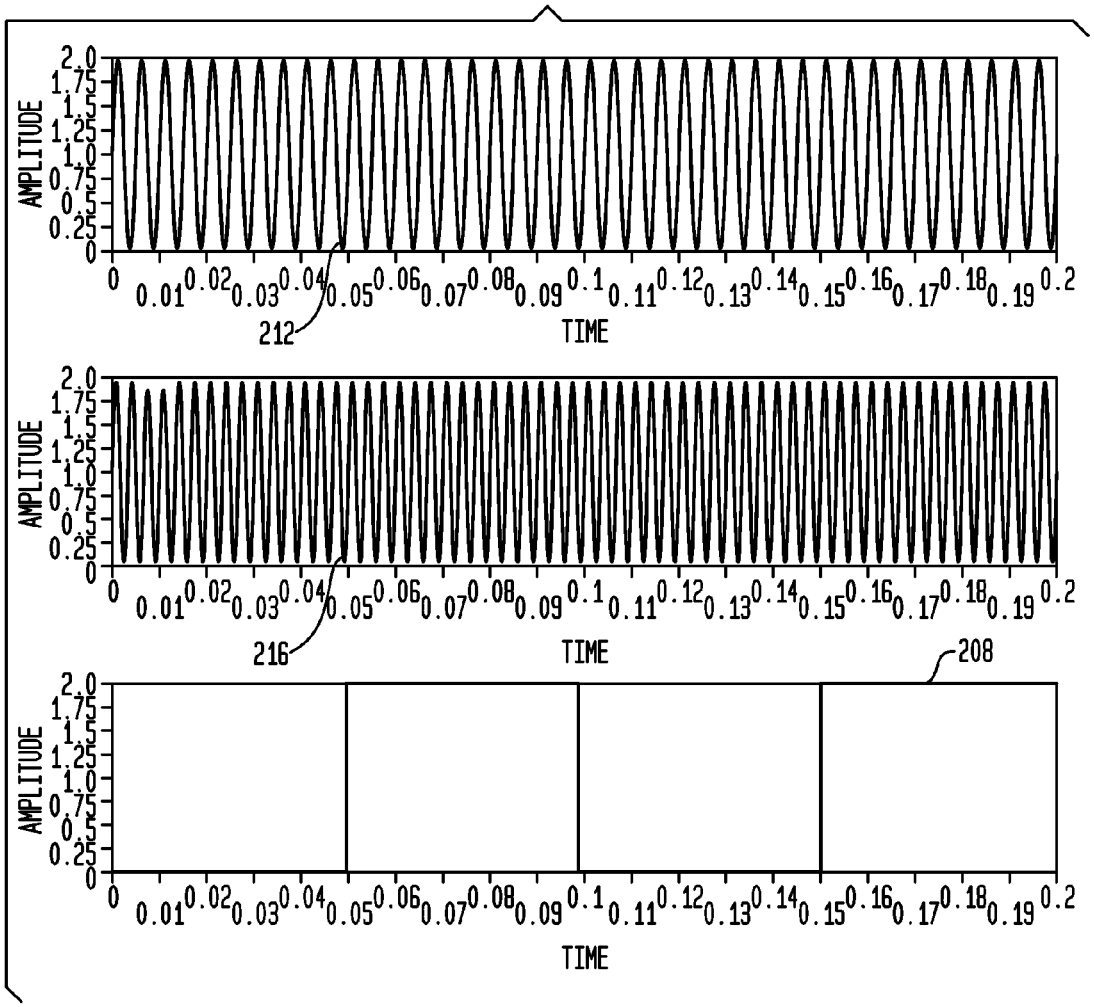
FIGS. 6A, 6B and 7 show exemplary waveforms generated by the device of FIG. 5.
Figure 6B:
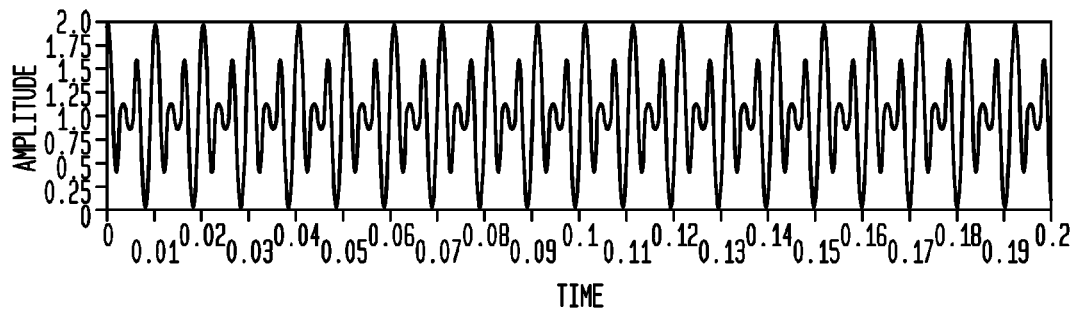

Referring to FIGS. 5, 6A, and 6B, in one embodiment of the present invention, the first waveform generator 206 generates the first waveform 208 or signal having a frequency known to stimulate a first selected body part, such as distal dorsal root nerve fibers within a specific dermatome. In one embodiment, the first waveform 208 may have a frequency of about 10-200 Hz and more preferably about 10-30 Hz, which are suitable frequency ranges for stimulating nerves. As indicated above, it has been observed that it is difficult to pass these relatively low frequency signals through body tissue to reach certain target nerves with sufficient current density to stimulate the target nerves. To address this problem, the second waveform generator 210 generates a higher frequency first carrier waveform 212 of approximately 10-400 KHz and more preferably about 200 KHz, and the third waveform generator 214 generates another high frequency second carrier waveform 214 that is different than the first carrier waveform 212. For example, in one embodiment, the second carrier waveform 216 has a frequency of about 10-400 KHz, and more preferably about 300 KHz. Providing relatively high-frequency carrier waveforms having different frequencies will preferably produce a nerve stimulating signal that is capable of stimulating nerves at different depths. The first and second carrier waveforms 212, 216 are applied along with the first nerve stimulating waveform 208 to an amplitude modulator 218, such as an On-Semi MC1496 modulator sold by Texas Instruments.

Figure 7:
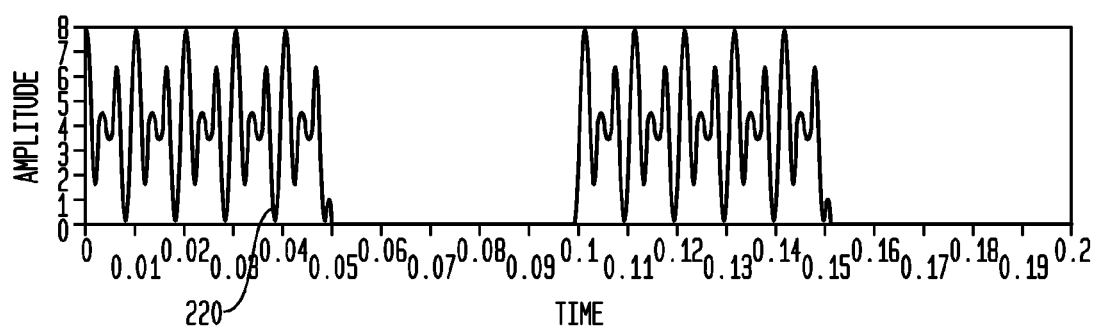

In one embodiment, the first waveform 208 is preferably a square wave having a frequency of approximately 10-30 Hz, the first carrier waveform 212 is preferably a sinusoidal signal having a frequency in the range of about 200 KHz, and the second carrier waveform 216 is preferably a sinusoidal signal having a frequency in the range of about 300 KHz. In other embodiments, other ranges may be used for the waveforms. Preferably, the first and second carrier waveforms 212, 216 have different frequencies. The signals shown in FIGS. 6A, 6B and 7 are for illustrative purposes only, and are not intended as true representations of the exemplary signals described herein. It is contemplated that other frequencies may be used and still fall within the scope of the present invention.

Referring to FIG. 5, in operation, the modulated signal 220 generated by modulator 218 is transmitted to electrode(s) 222, which, in turn, apply the modulated signal 220 to the target nerve(s) within a dermatomic region. As is readily understood by those skilled in the art, the use of the modulated signal 220 provides for efficient stimulation of the target nerve(s) due to the high frequency nature of the carrier waveform enabling the low frequency signal to be detected (and responded to) by the target nerve. Moreover, the carrier waveforms 212, 216 generate different frequencies, thereby passing through tissue at differing depths.

Figure 8:
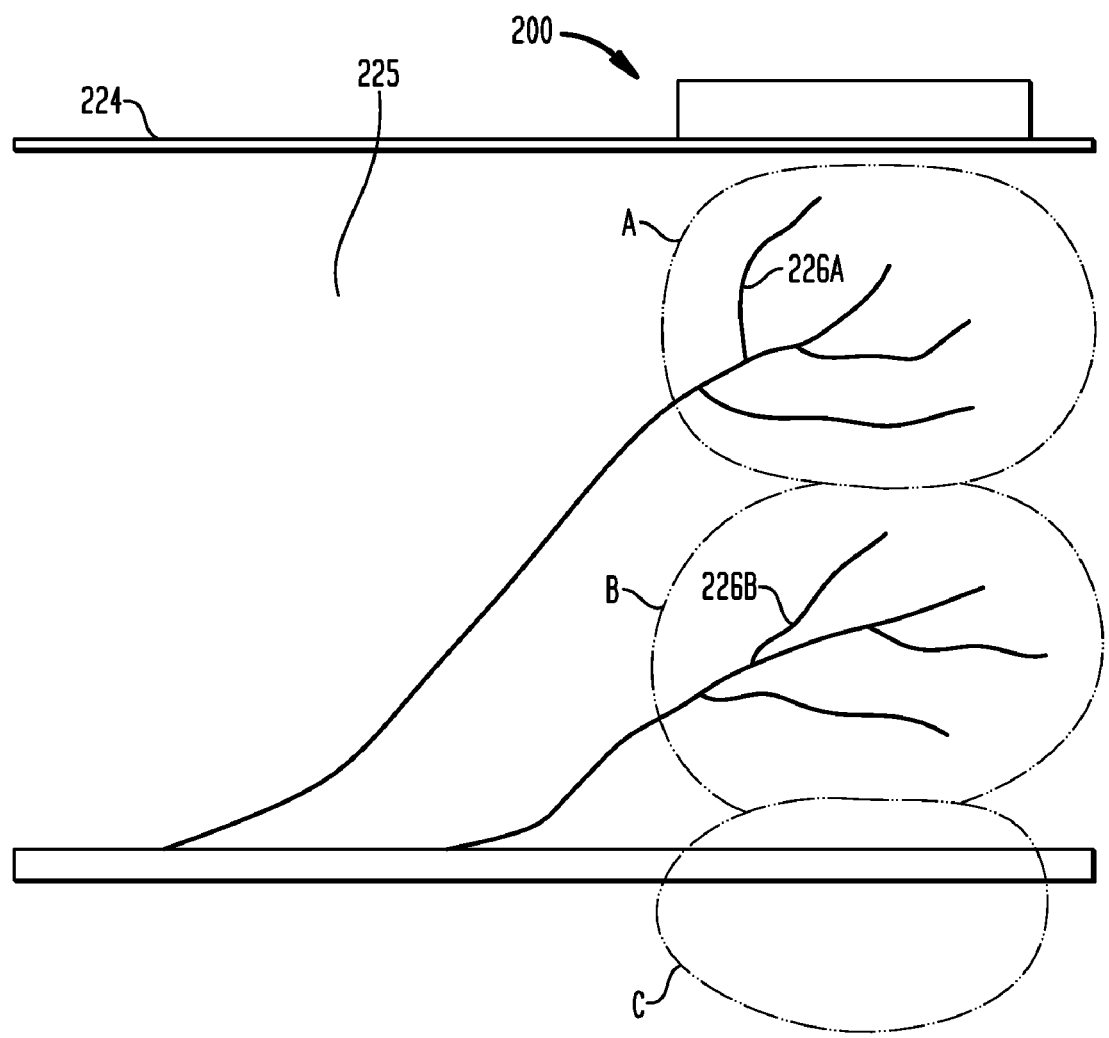
FIG. 8 shows a nerve stimulation device attached to the skin of a mammal, in accordance with one embodiment of the present invention.

FIG. 8 shows the nerve stimulation device 200 of FIG. 5 applied to the skin 224 of a mammal. The nerve stimulation device 200 generates the nerve stimulation waveform 220 shown in FIG. 7. The nerve stimulation waveform 220 includes a first part, which is a combination of the first waveform 208 and the first carrier waveform 212 and that is capable of passing through the tissue 225 of the mammal to reach the depth designated "A" so as to stimulate a first branch 226A of nerve fibers. The nerve stimulation waveform 220 also has a second part, which is a combination of the first waveform 208 and the second carrier waveform 216 and that is capable of passing through the tissue of the mammal to reach the depth designated "B" so as to stimulate a second branch 226B of nerve fibers. Other carrier waves having other frequencies may be added to stimulate nerves at other depths within the tissue.

Although the present invention is not limited by any particular theory of operation, it is believed that electrical stimulation on the skin surface, over the area of a dermatome, will generate action potentials within the nerve fibers that feed back into the dorsal root ganglion, and ultimately the dorsal root itself. Stimulation with only low frequency, (10-200 Hz), and relatively low energy levels, (10-30 micro amp signals), such as those found in conventional TENS devices, will not penetrate to deeper branches of the distal dorsal root fibers as the electrical impedance of the skin and tissues will resist the flow of energy. As the skin is made up of different layers, including the epidermis, dermis, and subcutaneous layers, electrical stimulation of the skin via a low frequency signal (TENS) will result in considerable energy dissipation within the top epidermal layer of the skin due to well-understood capacitive effects. When more energy is used to overcome impedance and reach the nerves at deeper layers, significant adverse circumstances arise such as vibration of the skin surface.

To overcome these tissue impendence problems, and to stimulate deeper distal dorsal root nerve fibers, the amplitude of the signal must increase or the frequency may be adjusted. As described herein, high frequency signals will travel deeper into the tissue of the body but will not stimulate nerves. However, modulating a high frequency signal with a low frequency pulse envelope will effectively stimulate nerves. That is, utilization of the modulated signal with its high frequency carrier effectively bypasses the capacitive layers of the electrode/skin interface and epidermis, thereby enabling direct stimulation of sensory nerve endings within the dermis. Moreover, using high frequency carrier waveforms having different frequencies (e.g. 200 KHz and 200 KHz) will enable nerve stimulation at different depths. Collateral skin effects and the energy required to stimulate nerve endings within the dermis are minimized.

In one embodiment of the present invention, the frequency of the carrier waveform may be adjusted to deliver the stimulus waveform just deep enough to instigate an action potential of the distal dorsal root nerve fibers of a dermatomic region, but not deep enough to stimulate other peripheral nerves. That is, altering the carrier frequency of the nerve stimulation signal will produce different waveforms that can be measured at varying depths. Furthermore, a plurality of overlapping signals may produce a specifically defined field of waveforms that bathe the nerve roots with increasing depth. In one embodiment of the present invention, a nerve stimulation device generates two carrier waveforms within a single pulse envelope, one transmitting at 200 KHz and the other at 300 KHz. By transmitting these waveforms simultaneously, the waveforms are in essence added, resulting in a single waveform. The new combined waveform has spectral components of the two separate carrier waveforms at 200 KHz and 300 KHz. Further, amplitude modulation of the complex waveform with a low frequency component, for example a frequency of 10 Hz, results in a pulsed complex waveform. Thus, by using these carrier waveforms at differing frequencies, but transmitting them simultaneously, nerves at different depths within a dermatome may be stimulated. These waveforms will create a field that stimulates all distal dorsal root nerve fibers within a specific dermatome to various depths, not just those at the skin surface. Moreover, by controlling the frequency of the carrier waveforms, the nerve stimulating signals will be carried to target nerves, while not stimulating non-targeted nerves. The use of the modulated signals described herein enables transmission of the waveform into the skin and allows it to be detected (and responded to) by the predetermined nerve ending within the specific dermatome.

In one embodiment of the present invention, a third carrier waveform may be used. The third carrier waveform may be added to the first two carrier waveforms as described above, and create a complex waveform with spectral components of the three separate carrier waveforms. In yet another embodiment, the shape of the modulated waveform may change. For instance, the modulation waveform may be a triangular waveform with numerous carrier waveforms within it as described above.

Although one specific embodiment has been described thus far, those skilled in the art will recognize that the appropriate signals may be manipulated in many different ways to achieve suitable modulated signals and/or signal packages. For example, referring to FIG. 9, in one embodiment of the present invention, a nerve stimulation device 300, such as a transdermal patch 302, is powered by a battery 304. The nerve stimulation device 300 has a first waveform generator 306 adapted to generate a first waveform 308 having a frequency capable of stimulating a predetermined nerve of the mammal, a second waveform generator 310 adapted to generate a first carrier waveform 312 having a frequency capable of passing through the tissue of the mammal, a third waveform generator 314 adapted to generate a second carrier waveform 316 having a frequency capable of passing through the tissue of the mammal, and a fourth waveform generator 335 adapted to generate a third carrier waveform 337 having a frequency capable of passing through the tissue of the mammal. The device preferably includes a modulation device 318 electrically coupled to the first, second, third, and fourth waveform generators 306, 310, 314, and 335 that is adapted to modulate the first waveform 308, and the carrier waveforms 312, 316, and 337 to create a modulated waveform 320, and an electrode 322 electrically coupled to the modulation device 318 and positioned substantially adjacent to the skin of the mammal for applying the modulated waveform 320 thereto.

Figure 9:
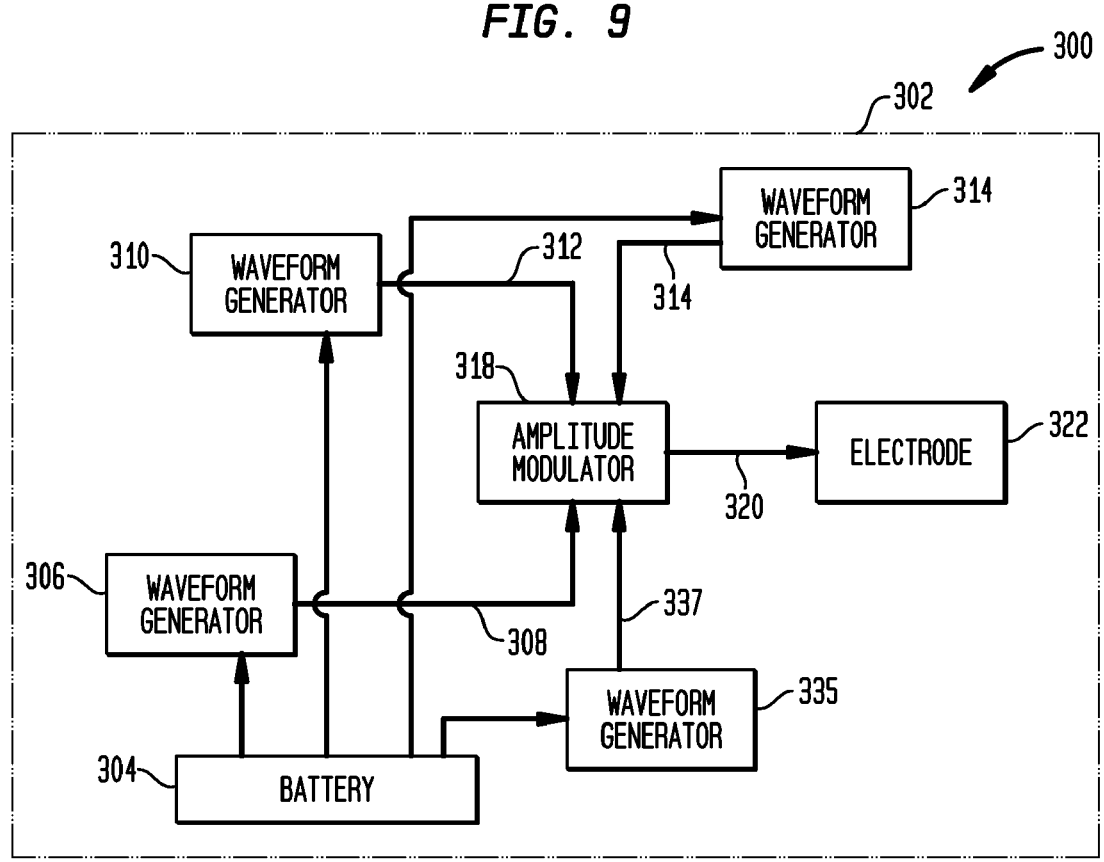
FIG. 9 shows a schematic illustration of a nerve stimulation device, in accordance with another preferred embodiment of the present invention.
Figure 10:
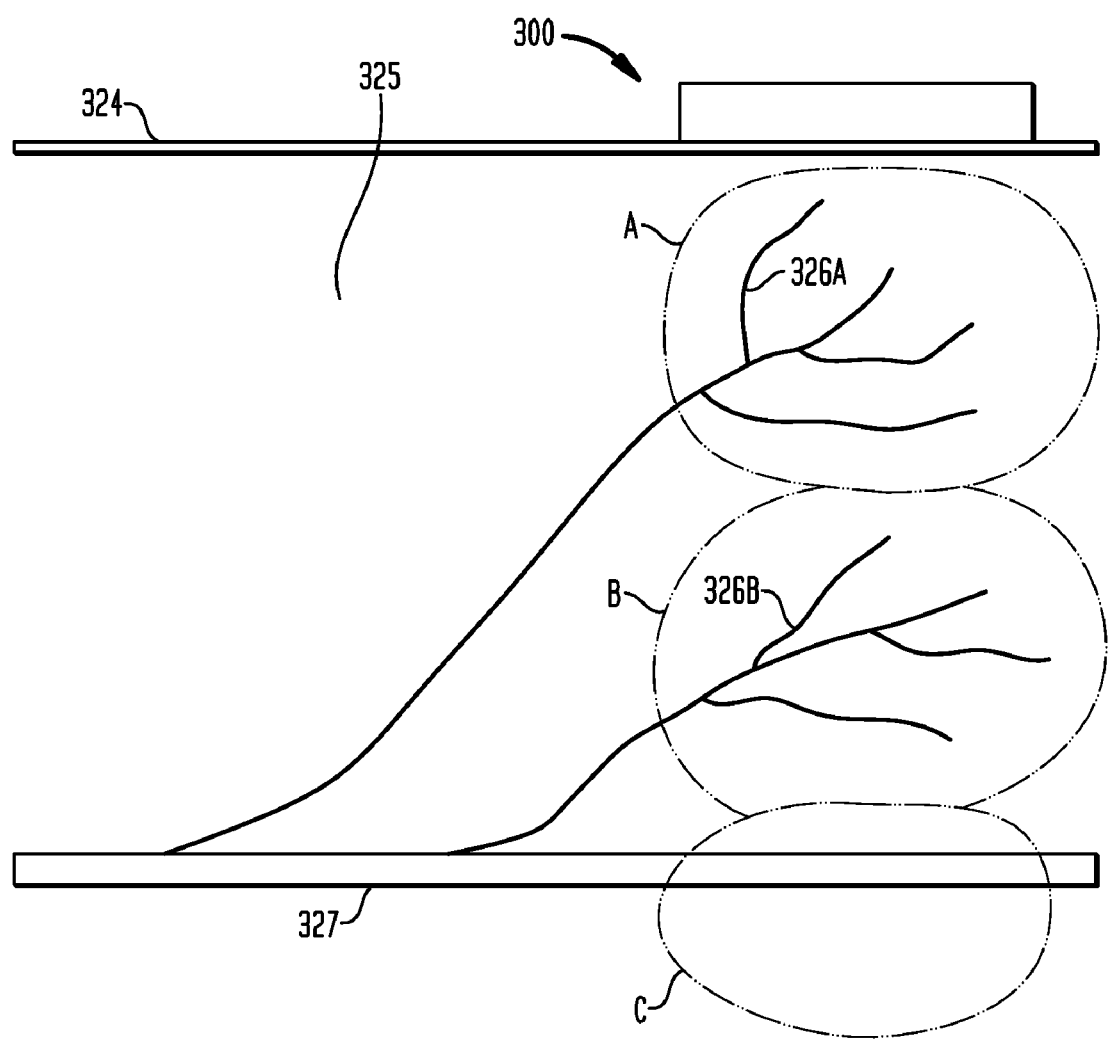
FIG. 10 shows a nerve stimulation device attached to the skin of a mammal, in accordance with one embodiment of the present invention.

Referring to FIGS. 9 and 10, in one embodiment of the present invention, a nerve stimulation device 300 generates a first signal portion combining first waveform 308 and first carrier waveform 312 that is capable of passing through the tissue 325 of the mammal to reach the depth designated "A" so as to stimulate a first branch 326A of nerve fibers. The nerve stimulation device 300 generates a second signal portion that combines first waveform 308 with second carrier waveform 316 that is capable of passing through the tissue of the mammal to reach the depth designated "B" so as to stimulate a second branch 326B of nerve fibers. In addition, the nerve stimulation device 300 generates a third signal portion that combines the first waveform 308 with the third carrier waveform 337, and that is capable of passing through the tissue of the mammal to reach the depth designated "C" so as to stimulate the distal end 327 of a dorsal root. Thus, the device shown in FIGS. 9 and 10 is able to stimulate different parts of a nerve at different depths, which is believed to enhance the efficacy of the nerve stimulating treatment. In one embodiment, the nerve stimulating signals are transmitted simultaneously to different depths so as to stimulate different nerve branches at the same time. In one embodiment, the nerve stimulation signals may be transmitted to different depths in a sequential or rotating pattern. In another embodiment, groups of nerve branches, with each nerve branch being at a different depth, may be stimulated in a sequential or rotating pattern. For example, a first group of nerve branches may be stimulated while a second group of nerve branches is not stimulated, and then the second group may be stimulated while the first group is not stimulated. This pattern of stimulation may be rotated back and forth between the two groups. Other embodiments may incorporate a third, fourth or more groups of nerve branches for the sequential or rotating pattern.

Although the present invention is not limited by any particular theory of operation, it is believed that stimulating the outer branches of a root nerve at different depths will lower the stimulation threshold normally required to stimulate the root nerve itself. In other words, it is believed that the devices and methods of the present invention provide techniques for "bathing" the entire depth of a nerve, which reduces the current required to stimulate the root nerve. This is because the aggregate effect of stimulating the outer nerve branches (e.g. afferent nerves) at various depths effectively lowers the threshold needed to stimulate the root nerve. As a result, effective root nerve stimulation may be achieved while using less power than would normally be required using prior art devices and methods. Moreover, the adverse consequences associated with prior art nerve stimulation devices such as high power consumption, skin vibration, pain, and unwanted stimulation of untargeted nerves and body parts may be avoided. Furthermore, the reduced power needs of the present invention will increase the length of time that a device may be used before replacing and/or recharging the power supply.

Figure 11:
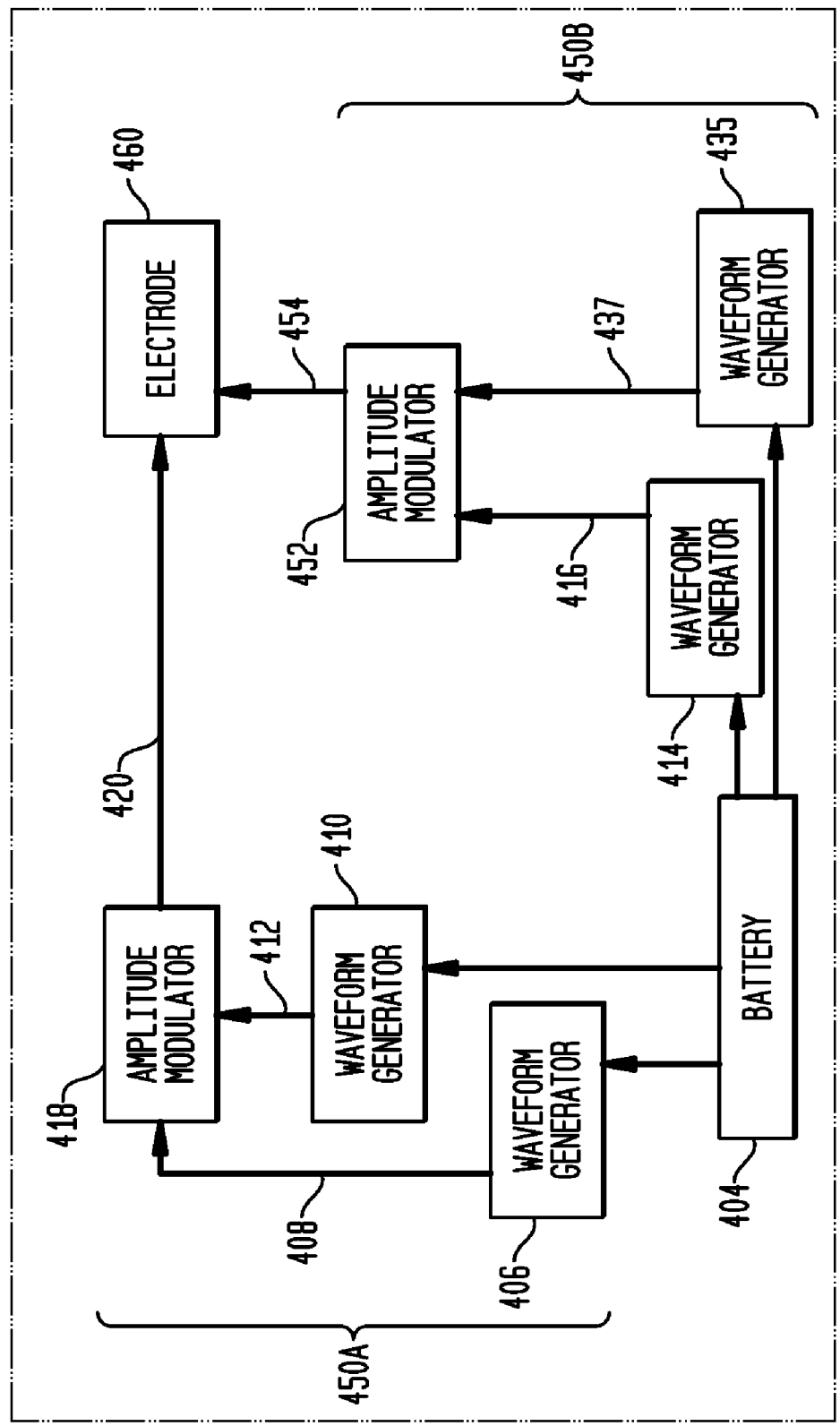
FIG. 11 shows a schematic illustration of a nerve stimulation device, in accordance with one embodiment of the present invention.

Referring to FIG. 11, in one embodiment of the present invention, a nerve stimulation device has two systems 450A, 450B. The first system 450A includes a first waveform generator 406 adapted to generate a first nerve stimulating waveform 408 having a frequency capable of stimulating a predetermined nerve of a mammal, and a second waveform generator 410 adapted to generate a first carrier waveform 412 having a frequency capable of passing through the tissue of the mammal. The first system 450A includes a modulation device 418 electrically coupled to the first and second waveform generators 406, 410 that is adapted to modulate the first and carrier waveforms 408, 412 to create a modulated waveform 420. The second system 450B includes a third waveform generator 414 adapted to generate a second nerve stimulating waveform 416 having a frequency capable of stimulating a predetermined nerve of the mammal, and a fourth waveform generator 435 adapted to generate a second carrier waveform 437 having a frequency capable of passing through the tissue of the mammal. The second system 450B includes a second modulation device 452 electrically coupled to the third and fourth waveform generators 414, 437 that is adapted to modulate the second nerve stimulating waveform 416 and the second carrier waveform 437 to create a modulated waveform 454. An electrode 460 is electrically coupled to the two modulation devices 418, 452, and is positioned substantially adjacent to the skin of the mammal for applying the modulated waveforms thereto. The carrier waveforms 412, 437 preferably have different frequencies, thereby passing through the tissue to different depths. In one embodiment, the first system 450A generates a carrier waveform at 200 KHz, which is modulated by a low frequency component at 10 Hz. Simultaneously, the second system 450B generates a carrier waveform at 300 KHz, which is modulated by a low frequency component at 10 Hz. The combination results in two modulated waveforms having different carrier frequencies that stimulate nerves at different depths. In other embodiments, the low frequency waveforms may have different frequencies.

In one embodiment of the present invention, stimulation of the S2 or S3 dermatome could be utilized to control fecal and/or urinary incontinence via activation of the S2 and S3 afferent parasympathetic pathways to the spinal cord. It has been observed that activation of the S2 and S3 afferent pathways results in inhibition of efferent pelvic motor nerves that innervate the descending colon and bladder by promotion of hypogastric nerve activity. Increased hypogastric nerve activity, causes colon and bladder relaxation. In one embodiment, the nerve stimulation device may be placed over the S2 or S3 dermatome to stimulate the hypogastric or pudendal nerves, at a location lower down the spine such as in the sacral region where those nerves exit the spinal column.

In one embodiment, a treatment for fecal/anal incontinence includes placing a relatively small device with two electrodes on the surface of the skin. The electrodes, each having a surface area of about one $cm^2$, are centered in a site two cm lateral of the midline of the spine at the level of S2-S3. A combined 200 KHz and 300 KHz sinusoidal carrier wave modulated by a 10 Hz square pulse waveform is transmitted at the site to stimulate afferent sensory nerve fibers, which connect to the S2-S3 dorsal root nerve fibers. In other embodiments, carrier waves having other frequencies may be used, such as carrier waves having frequencies within the range of 10-400 KHz.

In one embodiment, a nerve stimulation device is used to stimulate one or more of the T5-T9 dermatomes to enhance the perception of satiety. In this instance, the patch would preferably be placed over the back in the vicinity of the T5-T9 vertebra so as to target the T5-T9 dermatome, for stimulation of the celiac ganglia of the sympathetic nervous system.

In one embodiment, obesity may be treated using a nerve stimulation device having two electrodes that are placed on the surface of the skin. Electrodes, each having a surface area of about 1 $cm^2$, are centered in a site approximately six cm lateral to the midline of the spine at the level of T5-T9, running over the course of the rib. A combined 200 KHz and 300 KHz sinusoidal carrier wave modulated by a 10 Hz square pulse waveform is transmitted at the site to stimulate afferent sensory nerve fibers, which connect to the T5-T9 dorsal root nerve fibers.

In one embodiment of the present invention, a nerve stimulation device may be used for treating under active appetite disorders. This may be accomplished by stimulation of the celiac ganglia (using any of the devices disclosed herein) to induce changes in the parasympathetic nerves responsible for gastric emptying and appetite. Although the present invention is not limited by any particular theory of operation, it is believed that stimulating the celiac nerve plexus directly innervating the stomach may generate nerve impulses to the brain, which create the feeling of hunger. Second, the nerve stimulation may increase the activity of the gastric pacemaker and speed up peristalsis. Thus, the stomach empties quickly so that normal nerve impulses are generated that create the feeling of hunger.

For a given patient, the combination of current intensity, pulse frequency and pulse duration that induce greater appetite is different than the combination of current intensity, pulse frequency and pulse duration that would induce appetite suppression. While the exact combination necessary to bring about the desired result may vary in each patient, in general, greater stimulation for longer periods of time will slow down the activity of the gut to decrease and suppress appetite. If the desired effect is appetite suppression therefore, longer stimulation periods at higher current intensity, pulse frequency and/or pulse duration will tend to bring about this effect. Conversely, if the desired effect is greater appetite, shorter stimulation periods at lower current intensity, pulse frequency and/or pulse duration may tend to bring about this effect.

Referring to FIG. 12, in one embodiment of the present invention, a nerve stimulation device may include an implantable pulse generator 500 having a housing 502 that is implantable in a body of a mammal (e.g. a human). The implantable pulse generator (IPG) 500 includes a suitable power source 504, such as a lithium ion battery, a first waveform generator 506 that produces a first waveform 508, a second waveform generator 510 that produces a first carrier waveform 512, and a third waveform generator 514 that produces a second carrier waveform 516. The first, second, and third waveform generators 506, 510, and 514 are preferably electrically coupled to and powered by the battery 504. These waveform generators may be of any suitable type, such as those sold by Texas Instruments of Dallas, Tex. under model number NE555. The outputs of the respective first 506, second 510 and third 514 waveform generators are applied to an amplitude modulator 518, which modulates the three waveforms into a modulated signal package 520. The term "signal package" is used herein to describe a single output signal consisting or two or more individual signals modulated together in any way.

The first waveform generator 506 generates the first waveform 508 or signal having a frequency known to stimulate a first selected body part, such as the distal end of a nerve fiber. In one embodiment, this frequency is about 10-400 Hz and more preferably within the range of about 10-30 Hz. As indicated above, it has been proven difficult to pass such a low frequency signal through body tissue to reach certain target nerves with sufficient current density to stimulate the target nerves. To overcome this problem, the second waveform generator 510 generates a higher frequency first carrier waveform 512 (e.g. 10-400 KHz and more preferably about 200 KHz), and the third waveform generator 514 generates another high frequency second carrier waveform 516 (e.g. 10-400 KHz and more preferably about 300 KHz). The higher frequency carrier waveforms 512, 516 are applied along with the first waveform 508 to an amplitude modulator 518, such as an On-Semi MC1496 modulator sold by Texas Instruments. The two distinct carrier waveforms 512, 516 carry the nerve stimulating signal 508 to different tissue depths within a dermatomic region. One or more additional carrier waveforms may be added to carry the nerve stimulating waveform to other depths.

In operation, the modulated signal 520 generated by the modulator 518 is transmitted through lead 575 to electrodes 522. In turn, the electrodes 522 apply the modulated signal 520 to the target nerve fibers 526A, 526B. As is readily understood by those skilled in the art, the use of the modulated signal 216 provides for efficient stimulation of the target nerve fibers at different tissue depths due, in part, to the high frequency nature of the carrier waveforms enabling the low frequency signal to be detected (and responded to) by the target nerve fibers. In other embodiments, an implantable pulse generator may include any one of the features or elements disclosed herein.

In one or more embodiments of the present invention, the individual components of the modulated signal package may be used to selectively target different nerves, different nerve branches, different muscles, or selected other body parts. Thus, a single nerve stimulation device may provide stimulation signals designed to relieve different symptoms such as those associated with pain management, overactive bladder, fecal incontinence, interstitial cystitis and any other pelvic floor disorder. The nerve stimulation device may also be used to target nerve branches at different depths within the tissue of a mammal.

The invention disclosed herein is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although one embodiment of the present invention is described in relation to nerve stimulation in females, it is to be understood that it can be readily adapted for use in males, and children. The inventive principles, apparatus and methods disclosed herein may also have application for stimulating various other nerves, either independently or simultaneously, such as stimulation of nerves during labor and delivery, or selectively stimulating branches of a given nerve bundle to selectively address different patient conditions. Thus, the present invention can, for example, be used to selectively treat or affect one or more of the following conditions simultaneously: stress urinary incontinence, anal and fecal incontinence, pain, sexual dysfunction, interstitial cystitis, chronic pain such as but not limited to pelvic pain, nocturia, and gastrointestinal disorders such as but not limited to gastric pacing. Finally, the present invention as described herein can also be used to stimulate body parts other than nerves, such as glands that secrete hormones, and large muscle groups, such as biceps muscle stimulation associated with physical therapy.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A nerve stimulation device comprising:
a first waveform generator configured to generate a first waveform having a first frequency
capable of stimulating nerves within a dermatome;
a second waveform generator configured to generate a first carrier waveform having a
second frequency that is greater than said first frequency and that is capable of passing through tissue of a mammal;
a third waveform generator configured to generate a second carrier waveform having a
third frequency that is greater than said first frequency and that is different than said second frequency and being capable of passing through the tissue of the mammal;
a modulator electrically coupled to said first, second and third waveform generators and configured to modulate said first waveform, said first carrier waveform, and said second carrier waveform to generate a modulated signal package capable of stimulating the nerves at different depths within the dermatome, wherein the modulated signal package comprises a first part combining said first waveform and said first carrier waveform for stimulating a first branch of the nerves at a first depth within the dermatome, and a second part combining said first waveform and said second carrier waveform for stimulating a second branch of the nerves at a second depth within the dermatome; and an electrode electrically coupled to said modulator for applying said modulated waveform to the dermatome.

2. The nerve stimulation device as claimed in claim 1, further comprising a fourth waveform generator configured to generate a third carrier waveform having a fourth frequency capable of passing through the tissue of the mammal.

3. The nerve stimulation device as claimed in claim 2, wherein said modulator is electrically coupled to said fourth waveform generator to generate the modulated signal package comprising a third part combining said first waveform and said third carrier waveform for stimulating a third branch of the nerves at a third depth within the dermatome.

4. The nerve stimulation device as claimed in claim 1, wherein said first frequency of said first waveform is about 10-30 Hz, said second frequency of said first carrier waveform is about 200 KHz and said third frequency of said second carrier waveform is about 300 KHz.

5. The nerve stimulation device as claimed in claim 1, wherein said second frequency of said first carrier waveform is about 10-400 KHz.

6. The nerve stimulation device as claimed in claim 5, wherein said second frequency of said first carrier waveform is about 200 KHz.

7. The nerve stimulation device as claimed in claim 1, wherein said third frequency of said second carrier waveform is about 10-400 KHz.

8. The nerve stimulation device as claimed in claim 7, wherein said third frequency of said second carrier waveform is about 300 KHz.

9. The nerve stimulation device as claimed in claim 1, wherein said device comprises a transcutaneous nerve stimulation patch securable over skin, said patch including a circuitized substrate having said waveform generators and said electrode provided thereon.

10. The nerve stimulation device as claimed in claim 1, wherein said device comprises an electrode implantable in said mammal.

11. The nerve stimulation device as claimed in claim 1, wherein said device comprises an implantable pulse generator including an implantable housing.

12. A nerve stimulation device comprising:
a first system including
a first waveform generator configured to generate a first waveform having a first frequency
capable of stimulating nerves within a dermatome,
a second waveform generator configured to generate a first carrier waveform having a
second frequency that is greater than said first frequency and that is capable of passing through tissue of a mammal,
a first modulator electrically coupled to said first and second waveform generators and configured to modulate said first waveform, and said first carrier waveform to generate a first modulated waveform for stimulating a first branch of the nerves at a first depth within the dermatome;
a second system including
a third waveform generator configured to generate a second waveform having a third frequency that equals said first frequency of said first waveform and that is capable of stimulating the nerves within the dermatome, a fourth waveform generator configured to generate a second carrier waveform having a
fourth frequency that differs from said second frequency, that is greater than said third frequency, and that is capable of passing through the tissue of the mammal,
a second modulator electrically coupled to said third and fourth waveform generators and configured to modulate said second waveform, and said second carrier waveform to generate a second modulated waveform for stimulating a second branch of the nerves at a second depth within the dermatome; and
an electrode electrically coupled to said modulator for applying said first and second modulated waveforms, wherein said first and second modulated waveforms pass through the tissue at different depths for stimulating the nerves at different depths within the tissue.

13. The nerve stimulation device as claimed in claim 12, wherein said first frequency of said first waveform is about 10-200 Hz.

14. The nerve stimulation device as claimed in claim 12 wherein said second frequency of said first carrier waveform is about 10-400 KHz.

15. The nerve stimulation device as claimed in claim 12, wherein said third frequency of said second waveform is about 10-200 Hz.

16. The nerve stimulation device as claimed in 12, wherein said fourth frequency of said second carrier waveform is about 10-400 KHz.

17. The nerve stimulation device as claimed in claim 12, wherein said device comprises a transcutaneous nerve stimulation patch securable over skin.

18. The nerve stimulation device as claimed in claim 12, wherein said device comprises an implantable pulse generator including an implantable housing.

19. A method of stimulating nerves within a dermatome to different depths comprising:
generating a first waveform having a first frequency capable of stimulating the nerves within the dermatome;
generating a first carrier waveform having a second frequency that is greater than said first frequency and that is capable of passing through tissue within the dermatome;
generating a second carrier waveform having a third frequency different than said second frequency and greater than said first frequency and being capable of passing through the tissue within the dermatome;
combining said first waveform, said first carrier waveform, and said second carrier waveform to generate a modulated signal package capable of stimulating the nerves at two different depths within the dermatome; and
applying said modulated waveform to the dermatome for stimulating the nerves within the dermatome, wherein said modulated signal package comprises a first part combining said first waveform and said first carrier waveform for stimulating a first branch of the nerves at a first depth within the dermatome, and a second part combining said first waveform and said second carrier waveform for stimulating a second branch of the nerves at a second depth within the dermatome.

20. The method as claimed in claim 19, further comprising:
generating a third carrier waveform having a fourth frequency different than said second and third frequencies and being capable of passing through the tissue within the dermatome;
combining said third carrier waveform with said first waveform, said first carrier waveform, and said second carrier waveform to generate a second modulated signal package capable of stimulating the nerves at three different depths within the dermatome.

21. The method as claimed in claim 19, wherein said first waveform, said first carrier waveform, and said second carrier waveform are generated simultaneously.

22. The method as claimed in claim 19, wherein said first carrier waveform and said second carrier waveform are generated exclusively of one another.

23. The method as claimed in claim 19, wherein said first frequency of said first waveform is about 10-200 Hz, said second frequency of said first carrier waveform is about 10-400 KHz, and said third frequency of said second carrier waveform is about 10-400 KHz.

24. The method as claimed in claim 19, further comprising using a transcutaneous patch or an implantable device for applying said modulated waveform.

\* \* \* \* \*